United States Patent
Kiriyama et al.

(10) Patent No.: US 10,639,405 B2
(45) Date of Patent: May 5, 2020

(54) ADSORBENT FOR REMOVING HISTONE AND PURIFICATION DEVICE FOR LIQUID DERIVED FROM LIVING ORGANISM

(71) Applicant: ASAHI KASEI MEDICAL CO., LTD., Tokyo (JP)

(72) Inventors: Kentaro Kiriyama, Tokyo (JP); Satoru Inoue, Tokyo (JP); Yoshihiro Hatanaka, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 295 days.

(21) Appl. No.: 15/327,483

(22) PCT Filed: Jul. 21, 2015

(86) PCT No.: PCT/JP2015/070675
§ 371 (c)(1),
(2) Date: Jan. 19, 2017

(87) PCT Pub. No.: WO2016/013540
PCT Pub. Date: Jan. 28, 2016

(65) Prior Publication Data
US 2017/0173231 A1 Jun. 22, 2017

(30) Foreign Application Priority Data

Jul. 22, 2014 (JP) ................. 2014-148771
Sep. 17, 2014 (JP) ................. 2014-189364

(51) Int. Cl.
*A61M 1/02* (2006.01)
*A61M 1/38* (2006.01)
(Continued)

(52) U.S. Cl.
CPC ........ *A61M 1/0281* (2013.01); *A61M 1/3679* (2013.01); *A61M 1/38* (2013.01);
(Continued)

(58) Field of Classification Search
CPC .... A61M 1/0281; A61M 1/3679; A61M 1/38; B01D 15/362; B01J 20/20; B01J 20/261;
(Continued)

(56) References Cited

U.S. PATENT DOCUMENTS 4,886,836 A 12/1989 Gsell et al.
9,867,927 B2 * 1/2018 Tomita ................ A61M 1/3679
(Continued)

FOREIGN PATENT DOCUMENTS

EP 0267286 A1 5/1988
EP 0319144 A1 6/1989
(Continued)

OTHER PUBLICATIONS

Supplementary European Search Report dated Jul. 11, 2017 for family member EP 15825043.
(Continued)

*Primary Examiner* — John Kim
(74) *Attorney, Agent, or Firm* — Greenblum & Bernstein, P.L.C.

(57) ABSTRACT

Provided is an adsorbent for removing histones from a liquid derived from a living-organism, including a water-insoluble carrier and a biocompatible polymer. The carrier has activated carbon, a polyester, a polysulfone, or a cationic functional group. Also provided is a device for purifying a liquid derived from a living-organism to remove histones from a liquid derived from a living-organism, which has a housing equipped with an inlet and an outlet for the liquid derived from the living-organism and the above-described adsorbent housed in the housing. The liquid derived from the living-organism is moved through the housing of device for purifying the liquid derived from the living-organism to remove histones from the liquid derived from the living-organism.

17 Claims, 2 Drawing Sheets

(51) Int. Cl.

| | | |
|---|---|---|
| *B01D 15/36* | (2006.01) | |
| *B01J 20/26* | (2006.01) | |
| *B01J 20/28* | (2006.01) | |
| *B01J 20/32* | (2006.01) | |
| *B01J 47/016* | (2017.01) | |
| *A61M 1/36* | (2006.01) | |
| *B01J 20/20* | (2006.01) | |

(52) U.S. Cl.
CPC ............ *B01D 15/362* (2013.01); *B01J 20/20* (2013.01); *B01J 20/261* (2013.01); *B01J 20/28016* (2013.01); *B01J 20/28023* (2013.01); *B01J 20/28033* (2013.01); *B01J 20/3204* (2013.01); *B01J 20/328* (2013.01); *B01J 20/3208* (2013.01); *B01J 20/3276* (2013.01); *B01J 20/3289* (2013.01); *B01J 47/016* (2017.01)

(58) Field of Classification Search
CPC ............ B01J 20/3204; B01J 20/3208; B01J 20/3276; B01J 20/328; B01J 20/3289; B01J 20/28016; B01J 20/28033; B01J 20/28023; B01J 47/016
See application file for complete search history.

(56) References Cited

U.S. PATENT DOCUMENTS

| | | | |
|---|---|---|---|
| 2002/0146413 A1 | 10/2002 | Brady et al. | |
| 2002/0159995 A1 | 10/2002 | Brady et al. | |
| 2006/0286084 A1 | 12/2006 | Morita et al. | |
| 2012/0226258 A1* | 9/2012 | Otto | A61M 1/1698 604/500 |
| 2013/0195792 A1 | 8/2013 | Chan et al. | |

FOREIGN PATENT DOCUMENTS

| | | |
|---|---|---|
| EP | 1273682 | 4/2003 |
| EP | 2865384 | 4/2015 |
| JP | S64-26656 | 1/1989 |
| JP | H05-49694 | 3/1993 |
| JP | H05-95999 | 4/1993 |
| JP | H08-71412 | 3/1996 |
| JP | 2005-104908 | 4/2005 |
| JP | 2007-92034 | 4/2007 |
| JP | 2013-523772 | 6/2013 |
| WO | 2001/77420 | 10/2001 |
| WO | 2013/146142 | 10/2013 |
| WO | 2013/191280 | 12/2013 |

OTHER PUBLICATIONS

Iba et al., "Neutrophil extracellular traps (NETs), damage-associated molecular patterns (DAMPs) and cell-death during sepsis," Nihon Kyukyu Igakukai Zasshi (a.k.a. Japanese Journal of Association for Acute Medicine), 2013, pp. 827-836, vol. 24, along with an English language excerpt.

Xu et al., "Extracellular histones are major mediators of death in sepsis," Nature Medicine, Nov. 15, 2009, pp. 1318-1322, vol. 15, No. 11.

Ito et al., "Analysis of dynamisim of novel mediator extracellular histone in sepsis," Grants-inAid for Scientific Research (grants-in-aid for academic research aid fund) research results report, Kagoshina University, May 31, 2013, pp. 1-6.

Naka et al., "The Removal of Cytokines by Continuous Hemofiltration (CHF) and Continuous Hemodiafiltration (CHDF)," Japanese Journal of Apheresis, 1999, pp. 48-52, vol. 18(1), including an English language summary.

International Search Report issued in International Patent Application No. PCT/JP2015/070675, dated Sep. 8, 2015, along with an English translation thereof.

International Preliminary Report on Patentability issued in International Patent Application No. PCT/JP2015/070675, dated Jan. 24, 2017, along with an English translation thereof.

* cited by examiner

ADSORBENT FOR REMOVING HISTONE AND PURIFICATION DEVICE FOR LIQUID DERIVED FROM LIVING ORGANISM

TECHNICAL FIELD

The present invention relates to an adsorbent for adsorbing histones in a liquid derived from a living-organism and the like and a device for purifying a liquid derived from a living-organism using the adsorbent.

BACKGROUND ART

Systemic inflammatory response syndrome (SIRS) is a systemic inflammatory state enhanced due to excessive release of a substance such as cytokine triggered by infection or the like. Eighteen million people die of this disease every year in the world, but there has been no effective therapy for it.

Although clinical trials for an anti-TNF-α antibody, IL-1Ra, and the like have so far been attempted in order to neutralize an excessively produced inflammatory cytokine in diseases accompanied with SIRS, they have not yet succeeded in certifying their effectiveness.

The reason why an attempt to treat SIRS using a single inflammatory cytokine as a target has not yet produced effective results is presumed because SIRS has various backgrounds or symptoms and not only one cytokine but also a very complicated cytokine network causes SIRS.

Therapeutic apheresis, such as blood filtration, for comprehensively removing substances that cause disease from the blood have conventionally attracted attentions and a technology of removing proteins including cytokines of a middle molecular weight range has been proposed. For example, there is an attempt of using therapeutic apheresis by filtration/dialysis to remove all the mediators involved in a complicated cytokine network. Effectiveness produced by a mechanism different from monoclonal antibody administration of a cytokine to multiple organ failure is considered but there is a limit to the amount removable by it.

There have recently been reports on an inflammatory cytokine adsorbent developed to remove from the blood these inflammatory cytokines adsorbed thereto to treat SIRS (refer to, for example, Patent Document 1).

Furthermore, study results showing that histones are very important as a substance that causes SIRS have recently been disclosed newly (refer to, for example, Non-patent Documents 1 and 2).

This can be verified from the facts that the blood histone level of SIRS patients is several ten times to several hundred times higher than that of the normal subjects and that inflammatory model mice recovered by the administration of a histone antibody (refer to, for example, Non-patent Document 3).

Histones are main proteins that constitute chromatin found in eukaryotes. Due to abundant basic proteins, they are charged with a positive charge. Histones allow deoxyribonucleic acid (DNA) having negative charges derived from a phosphoric acid group to wrap around them about 2 times and play a role of packaging folded long DNA molecules in their nuclei. Histones are classified into four families, that is, H2A, H2B, H3, and H4. A histone octamer consisting of two copies of each of these four histones and wrapped by DNA is called "nucleosome". On the other hand, histones to be bound to DNA between nucleosomes (linker DNA) are called "linker histones" and a typical one is called Histone H1.

These histones are known to be cationic and in fact, as disclosed in Patent Documents 2 and 3, they are target proteins to be removed by a basic adsorbent such as sulfated cellulose or hydroxyapatite.

CITATION LIST

Patent Document

Patent Document 1: Published Japanese Translation of PCT application No. 2013-523772
Patent Document 2: Japanese Patent Laid-Open No. 2007-92034
Patent Document 3: Japanese Patent Laid-Open No. H8-71412

Non-Patent Document

Non-Patent Document 1: Xu J1, Zhang X, Pelayo R, Monestier M, Ammollo C T, Semeraro F, Taylor F B, Esmon N L, Lupu F, Esmon C T, "Extracellular histones are major mediators of death in sepsis", Nature Medicine, 2009 Nov. 15, 1318-1321, 1.
Non-Patent Document 2: Toshiaki Iba, Miwa Murai, Isao Nagaoka, Yoko Tabe, "Neutrophil extracellular traps (NETs), damage-associated molecular patterns (DAMPs) and cell-death during sepsis", Nihon Kyukyu Igakukai Zasshi, 24, 827-36 (2013).
Non-Patent Document 3: Takashi Ito, Ikuro Maruyama, Grants-in-Aid for Scientific Research (grants-in-aid for academic research aid fund) research results report, "Analysis of dynamism of novel mediator 'extracellular histone' in sepsis".

SUMMARY

Technical Problem

Thus, histones essentially have a function necessary for the living body, but they are substances that are, in a disease state such as sepsis, excessively released out of cells, worsen the disease state, and cause the living body to die. Histones are however primary proteins constituting chromatin of eukaryotes and have a considerably important role of folding DNA molecules and housing them in their nucleus. Considering that they have, in cells, a function necessary for the living body, administration of a drug inhibiting the histone activity may cause serious side effects on the living body. There is therefore a demand for the development of a means capable of selectively removing extracellular histones undesirable for the living body. Removing histones by extracorporeal circulation is considered as a candidate, but it has the drawback that histones cannot be removed efficiently while retaining good biocompatibility, that is, without causing thrombogenesis.

For example, sulfated cellulose used for the adsorbent described in Patent Document 2 is presumed to cause thrombogenesis because its strong anionic property activates the XII factor and activates the blood coagulation cascade. Hydroxyapatite used for the adsorbent described in Patent Document 3 is known to have strong protein adsorbing property and it is presumed to remove useful blood proteins adsorbed thereto and cause thrombogenesis. It is needless to say that medical materials used for blood purification are required to have antithrombogenicity as one of biocompatibility factors. From the standpoint of antithrombogenicity, the adsorbents described in Patent Documents 2 and 3 are presumed to be unsuited for blood purification and have no biocompatibility.

Solution to Problem

The present inventors therefore have carried out an extensive investigation in order to provide a device for therapeutic apheresis that selectively removes histones adsorbed thereto from a liquid derived from a living-organism and is excellent in biocompatibility. As a result, it has been elucidated that a histone adsorbent having a biocompatible polymer can remove histones with good compatibility while suppressing attachment of blood platelets and not forming thrombus. The device for therapeutic apheresis having such a histone adsorbent can be used for the therapy for diseases caused by histones such as SIRS. In addition, by bringing such a histone adsorbent into contact with a liquid derived from a living-organism, histones in the liquid derived from the living-organism are adsorbed to the histone adsorbent with good biocompatibility and histones can be removed from the liquid derived from the living-organism. Thus, extracellular histones undesirable for the living body can be removed.

The present invention therefore provides a histone adsorbent and a device for purifying a liquid derived from a living-organism as shown below in (1) to (15).
(1) An adsorbent for removing a histone from a liquid derived from a living-organism, which comprises a water insoluble carrier and a biocompatible polymer, the carrier being any one of carriers comprising activated carbon, a polyester, a polysulfone and a cationic functional group, respectively.
(2) The adsorbent as described in (1), wherein the biocompatible polymer comprises a cationic functional group.
(3) The adsorbent as described in (1) or (2), wherein the carrier is in particle form, in non-woven fabric form, or in hollow fiber membrane form.
(4) The adsorbent as described in (1), wherein the carrier comprises a cationic functional group and either one of polyethylene terephthalate or a styrene divinylbenzene-based copolymer.
(5) The adsorbent as described in (4), wherein the cationic functional group is an amino group.
(6) The adsorbent as described in (5), wherein the amino group is a quaternary ammonium group.
(7) The adsorbent as described in any of (1) to (6), wherein the biocompatible polymer is a hydrophilic polymer.
(8) The adsorbent as described in (7), wherein the hydrophilic polymer is a hydroxyethyl methacrylate-based polymer.
(9) The adsorbent as described in any of (1) to (7), wherein the biocompatible polymer is a polymer containing 10 mol % or more of dimethylaminoethyl methacrylate.
(10) The adsorbent as described in any of (1) to (9), wherein the histone is Histone H3.
(11) A device for purifying a liquid derived from a living-organism to remove a histone from the liquid derived from the living-organism, which comprises a housing equipped with an inlet and an outlet for a body liquid and the adsorbent as described in any of (1) to (10) housed in the housing, wherein the histone is removed from the liquid derived from the living-organism by moving the liquid derived from the living-organism through the housing.
(12) The device for purifying the liquid derived from the living-organism as described in (11), wherein the liquid derived from the living-organism is a body liquid.
(13) The device for purifying the liquid derived from the living-organism as described in (12), wherein the body liquid is the blood.
(14) A method of removing a histone, including using the device described in any of (11) to (13) to remove a histone from the liquid derived from the living-organism.
(15) A method of treating systemic inflammatory response syndrome, including allowing the blood or plasma to pass through the device described in any of (11) to (13) to reduce a histone content in the blood or plasma, respectively.

Advantageous Effects of Invention

According to the present invention, a histone adsorbent and a device for purifying a liquid derived from a living-organism capable of suppressing thrombogenesis and removing histones are provided.

DESCRIPTION OF EMBODIMENTS

Figure 1:
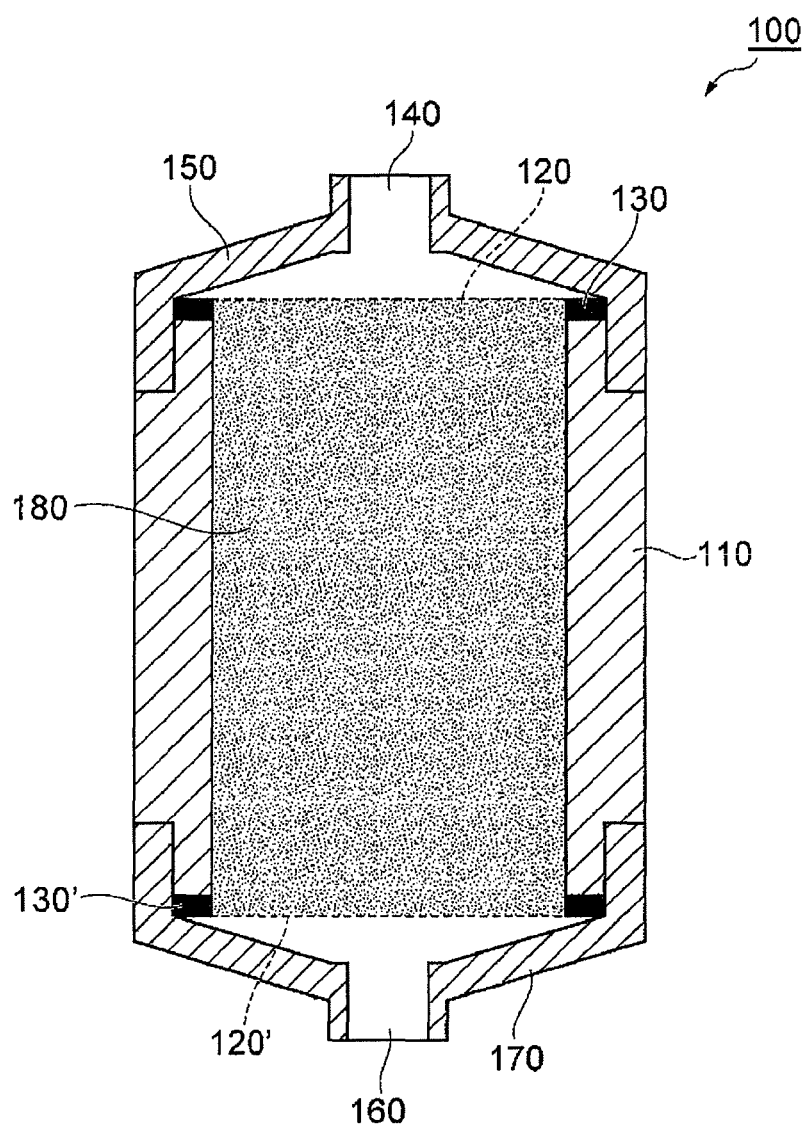
FIG. 1 is a cross-sectional view showing one embodiment of a device.

A preferable embodiment of the present invention (which will hereinafter be called "present embodiment") will next be described in detail. It is to be noted that the present embodiment shown below is only an example of a device or method for materializing the technical concept of the present invention and does not specify the combination of constituent members or the like to the following ones. The technical concept of the present invention can be modified in various ways within the claims.

An adsorbent according to the present embodiment is an adsorbent for removing histones from a liquid derived from living-organism and comprises a water insoluble carrier and a biocompatible polymer. The carrier of the adsorbent is composed essentially of activated carbon, a polyester, or a polysulfone or comprises a cationic functional group. A device for purifying the liquid derived from the living-organism according to the present embodiment is a device for purifying the liquid derived from the living-organism to remove histones from the liquid derived from the living-organism. The device for purifying the liquid derived from the living-organism comprises a housing comprising an inlet and an outlet for the liquid derived from the living-organism and the above-described adsorbent for removing histones from the liquid derived from the living-organism. The device removes histones from the liquid derived from the living-organism by moving the liquid derived from the living-organism through the housing.

(Water Insoluble Carrier)

The carrier which the adsorbent according to the present embodiment comprises is insoluble in water. Since the carrier is insoluble in water, elution of the carrier into the blood can be prevented when the adsorbent is brought into contact with the blood. In the present embodiment, the term "water insoluble" means that a weight loss of the adsorbent after it is dried for 24 hours, immersed in pure water for 24 hours, taken out from the pure water, and then dried at 60° C. for 24 hours is 10.0 wt. % or less.

(Material of Carrier)

As the material of the carrier insoluble in water, activated carbon-based materials (which may be called "activated carbon", simply), polyester-based ones (which may be called "polyester", simply), and polysulfone-based ones (which may be called "polysulfone", simply) can be used. Using an activated carbon-based, polyester-based, or polysulfone-based material is likely to provide industrial products in excellent productivity.

When the carrier is modified with a cationic functional group, any of known polymers capable of having a porous structure and insoluble in water can be used as the material of the carrier. Examples include activated carbon, styrene divinylbenzene-based, polyamide-based, polyester-based, polyurethane-based, polysulfone-based, polystyrene-based, polyethylene-based, polypropylene-based, cellulose-based, cellulose acetate-based, poly(meth)acrylate-based, polyacrylonitrile-based, and poly(methyl methacrylate)-based polymers, polymers of a vinyl compound such as ethylene vinyl alcohol copolymer, cellulose-based gel, dextran-based gel, agarose-based gel, polyacrylamide-based gel, and porous glass. Of these, the carrier using an activated carbon-based material, a polyester-based material such as polyethylene terephthalate (PET), a polysulfone-based material, and a styrene divinylbenzene-based material (which may be called "styrene divinylbenzene", simply) can provide industrial products in excellent productivity and the like.

The term "polyester-based material" as used herein means a polycondensate between a polyvalent carboxylic acid (dicarboxylic acid) and a polyalcohol (diol). Examples include PET, polybutylene terephthalate (PBT), polytrimethylene terephthalate, polyethylene naphthalate, and polybutylene naphthalate. From the standpoint of productivity of industrial products, PET and PBT are particularly preferred.

The term "polysulfone-based polymer" means a polyaryl ether sulfone polymer characterized by a structure including a recurring unit represented by the following chemical formula (1). Examples of the polysulfone-based polymer include polymers having a recurring unit represented by the following chemical formula (1) and polymers having a recurring unit represented by the following chemical formula (2):

[Chemical formula 1]

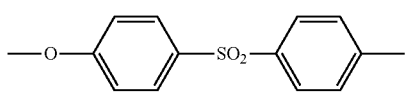

(1)

[Chemical formula 2]

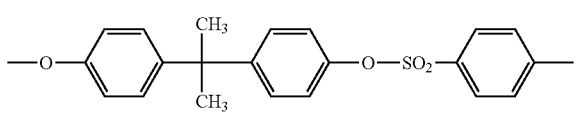

(2)

The term "styrene divinylbenzene-based polymer" means a copolymer obtained by mixing styrene with divinylbenzene to copolymerize them. It is a styrene divinylbenzene copolymer having a styrene skeleton crosslinked by divinylbenzene. Examples of the styrene divinylbenzene-based polymer include polymers having a recurring unit represented by the following formulas (3) and (4).

[Chemical formula 3]

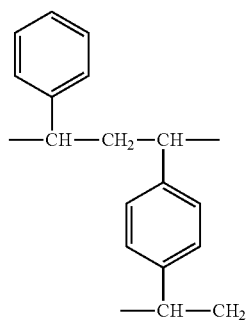

(3)

[Chemical formula 4]

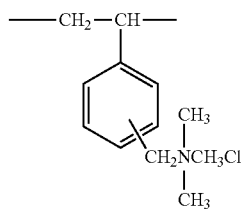

(4)

(Form of the Carrier)

The form of the carrier is not particularly limited and the carrier may be in any of the following forms: particle, hollow fiber, nonwoven fabric, fiber, sheet, and sponge. The carrier in particle form is likely to have a preferable contact surface area with a liquid derived from living-organism.

As the material of the carrier in particle form, any of the above-described materials may be used for the carrier. Using activated carbon or styrene divinylbenzene-based beads facilitates control of the pore size or surface area. In addition, they are likely to secure safety such as sterilization resistance or the like when the product is used as a medical device.

As the material of the carrier in nonwoven fabric form, any of the above-described materials may be used for the carrier. Of these, PET nonwoven fabric and PBT nonwoven fabric facilitate securing of safety such as sterilization resistance when the product is used as a medical device and in addition, they are likely to improve productivity in obtaining it as an industrial product.

As the material of the carrier in hollow fiber form, any of the above-described materials may be used for the carrier. Of these, polysulfone-based polymers, ethylene vinyl alcohol copolymers, and poly(methyl methacrylate)-based polymers facilitate securing of safety such as sterilization resistance when they are used as a medical device and in addition, they are likely to improve productivity in obtaining it as an industrial product.

The carrier in particle form has preferably an average particle size of from 50 to 1500 µm in consideration of its specific surface area and flowability of the liquid derived from the living-organism. When the whole blood is passed through the carrier, the carrier having an average particle size of from 100 to 1000 µm is more preferred. The term "particle size" as used herein means a length of the longest line among lines joining any two points on the outline of the carrier when it is observed under a microscope. The term "average particle size" means an arithmetic average particle size of 100 carrier particles selected at random.

The carrier in particle form has preferably a surface area of 1 m²/g or more, particularly preferably 5 m²/g or more from the standpoint of securing sufficient histone adsorbing capability. The surface area of the carrier can be measured, as described later, after removal of a coating polymer from the adsorbent.

The term "surface area" of the adsorbent means a surface area calculated, after measuring a nitrogen adsorption isotherm at liquid nitrogen temperature (77 K), using the BET (JIS Z 8830; determination of the specific surface area of powders (solids) by gas adsorption) analysis method. The nitrogen adsorption isotherm can be measured by two methods, that is, the volumetric method which determines the amount of nitrogen adsorbed to the carrier from a pressure reduction of a nitrogen gas that has filled a cell and the gravimetric method which determines weight variation of the carrier. Either of the two can be used for the measurement. Any method can be used insofar as it can measure the surface area.

When the carrier in hollow fiber form is used, the hollow fiber has an inner diameter of preferably from 10 to 1000 μm, more preferably from 100 to 300 μm from the standpoint the blood flows through the hollow fiber.

The term "hollow fiber inner diameter" as used herein means an average diameter determined by sampling some of hollow fibers constituting a filter carrier and observing the photograph of them through an electron microscope.

When the carrier is in nonwoven fabric form or in fabric form, the average fiber diameter of it can be set at from 0.3 μm to 10 μm. It is preferably from 0.3 μm to 3 μm, more preferably from 0.5 μm to 1.8 μm. When the average fiber diameter is 0.3 μm or more, a pressure loss during blood filtration becomes appropriate and hemolysis of erythrocytes is unlikely to occur.

The term "average fiber diameter" as used herein means an average diameter determined by sampling a portion of the nonwoven fabric or woven fabric constituting a filter carrier and observing the photograph of it through an electron microscope.

Examples of these carriers will next be described. Examples of the carrier in particle form include organic carriers, for example, carriers such as Diaion (product of Mitsubishi Chemical), Asahi Kasei Microcarrier (product of Asahi Kasei), and CM-Celluiofine (registered trademark) CH (exclusion limit protein molecular weight: about 3×10⁶, marketed by Seikagaku Corporation), polyvinyl alcohol-based carriers such as totally porous activated gel as described in Japanese Patent Publication No. H1-44725 and CM-Toyopearl (registered trademark) 650C (exclusion limit protein molecular weight: 5×10⁶, product of Tosoh Corporation), polyacrylamide-based carriers such as CM-Trisacryl M (CM-Trisacryl M) [exclusion limit protein molecular weight: 1×10⁷, product of Pharmacia-LKB/Sweden (Pharmacia-LKB)], and agarose-based carriers such as Sepharose CL-4B (Sepharose CL-4B) [exclusion limit protein molecular weight: 2×10⁷, product of Pharmacia-LKB/Sweden, (Pharmacia-LKB/Sweden)]; and inorganic carriers, for example, porous glass such as CPG-10-1000 [exclusion limit protein molecular weight: 1×10⁸, average pore size: 100 nm, product of Electro-nucleonics/USA (Electro-nucleonics)].

Examples of the carrier in hollow fiber form include APS (product of Asahi Kasei Medical), KF-C (product of Asahi Kasei Medical), TORAYLIGHT NV (product of Toray), YHF (product of Yuasa Membrane System), and STER-APORE (product of Mitsubishi Rayon Aqua Solutions).

Examples of the carrier in nonwoven fabric form include Sepacell (product of Asahi Kasei Medical), Bemliese (product of Asahi Kasei Fibers & Textiles SBU), Eltas (product of Asahi Kasei Fibers & Textiles SBU), Microweb (product of Asahi Kasei Fibers & Textiles SBU), Axtar (product of Toray), Clarex (product of Kuraray), Delpore (product of Sansho Co.), and Shyfine (product of Toyobo Co.).

(Biocompatible Polymer)

The adsorbent to be used for blood purification, which is inevitably brought into contact with the blood, has preferably, on the surface thereof, biocompatibility and has preferably a layer covered with a biocompatible polymer in order to prevent a useless reaction in the blood as much as much as possible. The term "biocompatibility" as used herein means, for example, a state in which the adsorbent is not recognized as a foreign matter by the blood. The adsorbent having a biocompatible surface is effective for disturbing thrombogenesis, for example, because attachment of erythrocytes or leukocytes to it is suppressed.

The adsorbent of the present embodiment has a carrier and a biocompatible polymer. The term "biocompatible polymer" as used in the present embodiment means a polymer present on the surface of the carrier of the adsorbent and therefore providing the adsorbent with improved biocompatibility. More specifically, it means a biocompatible polymer physically coated or chemically bound to the carrier of the adsorbent and thereby providing the carrier with improved antithrombogenicity compared with the carrier which has not yet been imparted with the biocompatible polymer.

Whether at least a portion of the polymer included in the adsorbent is a biocompatible polymer or not can be evaluated by the following procedure.

1) In a case where the polymer is a physically coated one:

After measurement of the antithrombogenicity of the adsorbent, the polymer included therein is dissolved in a proper solvent such as dimethylsulfoxide. After removal of the polymer from the adsorbent and drying the resulting carrier for one hour or more in a desiccator of 60° C., the carrier is left to stand for one hour or more in the desiccator. Then, the antithrombogenicity of the carrier after removal of the polymer from the adsorbent is measured. When the antithrombogenicity of the adsorbent is compared with the antithrombogenicity of the carrier and the following formula:

antithrombogenicity of adsorbent>antithrombogenicity of carrier after removal of polymer from adsorbent is satisfied, the polymer included in the adsorbent is a biocompatible polymer. It is to be noted that the antithrombogenicity is evaluated by observing the surface of the adsorbent macroscopically or by a scanning electron microscope and directly counting the number of platelets attached to the surface of the adsorbent or measuring the LDH activity of the blood cells attached to the surface of the adsorbent. When improvement in the antithrombogenicity of the adsorbent is evaluated compared with that of the carrier by either of the methods capable of measuring antithrombogenicity, the polymer included in the adsorbent is a biocompatible polymer.

When the polymer included in the adsorbent is dissolved in a proper solvent such as dimethylsulfoxide and then the polymer included in the adsorbent is identified by proton nuclear magnetic resonance (¹H-NMR) measurement or the like, the identified polymer corresponding to the biocompatible polymer exemplified below can be regarded as the biocompatible polymer. A polymer identification method is not limited to ¹H-NMR but any of the known identification methods can be used.

2) In a case where the polymer is a chemically bound one:

After measurement of antithrombogenicity of the adsorbent, the adsorbent was immersed temporarily in a strong acid and/or a strong alkali for a predetermined time to remove the polymer. Whether the biocompatible polymer is removed from the surface of the adsorbent or not can be confirmed by measuring a contact angle before and after treatment or carrying out surface analysis such as X-ray photoelectron spectroscopy (XPS) or the like. Then, the antithrombogenicity is evaluated using the above-described method. When the following formula:

antithrombogenicity of adsorbent>antithrombogenicity of carrier after removal of polymer from adsorbent is satisfied, the polymer included in the adsorbent is a biocompatible polymer.

The composition of the polymer can be estimated by totally judging the results of XPS, time-of-flight mass spectrometer (TOF-SIMS), and the like, but the measurement method is not limited thereto.

The histone adsorbent according to the present embodiment is only required to have, after imparted with the biocompatible polymer, histone adsorption capacity. The adsorbent according to the present embodiment also embraces that obtained by imparting a carrier originally having no histone adsorption capacity with a biocompatible polymer to allow it to express histone adsorption capacity.

As a method of producing the adsorbent including the biocompatible polymer, a known technology such as a method of imparting the surface of the carrier with the biocompatible polymer can be used.

Examples of the biocompatible polymer include monomers, polymers or graft copolymers having a polyalkylene glycol chain, ethylene-vinyl alcohol, polyester, poly-2-methoxyethyl acrylate (p-MEA), poly-2-methacryloyloxyethyl phosphorylcholine (PMPC), and polyvinylpyrrolidone (PVP). Of these, polymers having a hydroxyl group therein are preferred because they can prevent excessive trapping of platelets, with HEMA-based hydrophilic polymers such as polyhydroxyethyl methacrylate (p-HEMA) being particularly preferred. The HEMA-based polymers mean polymers containing HEMA in their polymer component and as another component, an arbitrary component can also be used. For example, the biocompatible polymer containing, as a monomer unit containing a basic nitrogen-containing portion, 10 mol % or more of dimethylaminoethyl methacrylate is likely to increase a histone removal ratio. From the standpoint of adsorbing histone and the like, the biocompatible polymer has preferably a cationic functional group. The cationic functional group will be described later.

(Amount of Biocompatible Polymer)

The amount of the polymer included in the adsorbent is calculated in the following procedure.

A carrier before having thereon the biocompatible polymer is dried for one hour or more in a desiccator set at 60° C. After the resulting carrier is left to stand for one hour or more in the desiccator, the weight of it is measured as A. Separately, a carrier having thereon the biocompatible polymer is dried for one hour or more in a desiccator set at 60° C. After the resulting carrier is left to stand for one hour or more in the desiccator, the weight of it is measured as B. The weights A and B are in gram. The amount of the polymer is calculated based on the following calculation formula:

Amount of polymer(mg/g carrier)=$(B-A) \times 1000/A$

The amount of the polymer can also be calculated in the following procedure.

The adsorbent is dried in a desiccator set at 60° C. for one hour or more. After the resulting adsorbent is left to stand in the desiccator for one hour or more, the weight of it is measured as C. Separately, the biocompatible polymer is dissolved in a proper solvent such as dimethylsulfoxide and dried in a desiccator set at 60° C. for one hour or more. Then, the resulting polymer is left to stand in the desiccator for one hour or more and the weight of it is measured as D. The weights C and D are in gram. The amount of the polymer is calculated based on the following calculation formula:

Amount of polymer(mg/g carrier)=$(C-D) \times 1000/D$

A molar ratio of monomer units contained in the biocompatible polymer containing many components can be determined from a $^1$H-NMR peak ratio obtained by dissolving coating polymer in a proper solvent such as dimethylsulfoxide and carrying out $^1$H-NMR measurement.

(Antithrombogenicity)

Antithrombogenicity can be studied by observing the surface of the adsorbent macroscopically or by a scanning electron microscope (SEM) and directly counting or quantifying, by image analysis, the number of platelets attached to the surface of the adsorbent.

In SEM observation, antithrombogenicity can be evaluated by the following procedure. First, the blood of the normal subject is circulated through a device including an adsorbent filled with physiological saline by a Perista™ pump for a predetermined time. Then, after washing the blood in the device including the adsorbent with physiological saline, the device is broken down and the adsorbent therein is taken out. After freeze drying of the adsorbent thus taken out, vapor deposition using ion sputter is performed. The SEM sample thus obtained is observed to evaluate its antithrombogenicity.

Alternatively, antithrombogenicity can be measured with an amount of platelets attached to the surface of the adsorbent as an indicator. For example, it can be determined by bringing a material into contact with PRP (Platelet rich plasma) in vitro for a predetermined time, treating platelets attached to the adsorbent with a surfactant, and measuring the lactate dehydrogenase (LDH) activity in the platelets. Since there is a strong correlation between the number of platelets attached to the material and the LDH activity, the number of platelets attached to the material can be determined from the LDH activity. In evaluation of antithrombogenicity using the whole blood, after the whole blood is brought into contact with the adsorbent for a predetermined time, the adsorbent is washed with physiological saline or buffer such as PBS to remove an erythrocyte component. Then, components other than the erythrocyte which are remaining on the surface of the material (mainly, platelets and leukocyte components) are treated with a surfactant and the activity of LDH thus eluted is measured. Thus, the antithrombogenicity of the adsorbent can be measured.

The following is a concrete method.

Evaluation of an adsorbent in non-woven fabric or particle form is made as follows:

1) Make a plurality of mini-modules equal in amount of an adsorbent. The term "mini-module" as used herein means a small-scale module made in a 1/200 scale of an actual product in order to evaluate the adsorbent using a small blood amount. For example, an adsorbent-filled column made by filling a laboratory column (MoBiTec) having an inner diameter of 9 mm and a volume of 2.5 mL with the adsorbent can be used.

2) Move physiological saline through the mini-module to wash it.

3) Move heparin-added human blood through the mini-module and then wash it with physiological saline.
4) Take the adsorbent from the mini-module thus washed and cause LDH to elute from the platelets in a Triton-X100 solution which is a surfactant.
5) LDH produces lactic acid when pyruvic acid is used as a substrate in the presence of β-Nicotinamide adenine dinucleotide reduced form (β-NADH) Therefore, measure a reduction rate of NADH from a change in absorbance at this time, calculate LDH activity, and convert it into the number of platelets. In the present method, the adsorbent is evaluated to have higher LDH activity when a reduction degree is larger, meaning that an amount of blood cells (mainly, platelets and leukocytes) attached to the surface of the adsorbent is larger.

Evaluation of an adsorbent in hollow fiber form is made as follows:
1) Make a plurality of mini-modules equal in membrane surface area. As this "mini-module", a column made by attaching both ends of a hollow fiber adsorbent with an epoxy adhesive so as to adjust the effective length to 15 cm and the membrane surface area to 50 mm$^2$ can be used.
2) Move physiological saline through the mini-module to wash it.
3) Move heparin-added human blood through the mini-module and then wash it with physiological saline.
4) Take the hollow fiber adsorbent from the mini-module thus washed and cause LDH to elute from the platelets in a Triton-X100 solution which is a surfactant.
5) LDH produces lactic acid when pyruvic acid is used as a substrate in the presence of β-Nicotinamide adenine dinucleotide reduced form (β-NADH). Therefore, measure a reduction rate of NADH from a change in absorbance at this time, calculate LDH activity, and convert it into the number of platelets. In the present method, the adsorbent is evaluated to have higher LDH activity when a reduction degree is larger, meaning that an amount of blood cells (mainly, platelets and leukocytes) attached to the surface of the adsorbent is larger.

(Cationic Functional Group)

Histone is cationic so that it has conventionally been thought to be one of target proteins to be separated and purified using an anionic adsorbent. The present inventors however have found that histone is adsorbed to a cationic material. The adsorbent therefore has, on the surface thereof, preferably a cationic functional group. For example, the material of the carrier may have a cationic functional group or the biocompatible polymer may have a cationic functional group. Examples of the cationic functional group to be introduced into the surface of the carrier include functional groups such as primary amino group, secondary amino group, tertiary amino group, imino group, and quaternary ammonium group. Preferably, a quaternary ammonium group is used. It is to be noted that the secondary amino group, the tertiary amino group, and the quaternary amino group may also be called a monoalkyl-substituted amino group, a dialkyl-substituted amino group, and a trialkyl-substituted amino group, respectively. The surface of the adsorbent may be made cationic by coating the carrier with a polymer containing the above-described cationic functional group. A carrier coated with the biocompatible polymer may be coated further with a polymer for introducing a cationic functional group. A carrier coated with a polymer for introducing a cationic functional group may be coated further with the biocompatible polymer. When coating is performed in stages, coating with a polymer having both properties, that is, biocompatibility and cationic functional group is preferred because the coating polymer of the first stage may elute during the second-stage coating.

(Amino Group)

Examples of the amino group include amino groups derived from compounds such as aminohexane, monomethylaminohexane, aminooctane, aminododecane, aminodiphenylmethane, 1-(3-aminopropyl)imidazole, 3-amino-1-propene, aminopyridine, aminobenzenesulfonic acid, tris(2-aminoethyl)amine, dimethylamine or diaminoethane, diethylenetriamine, triethylenetetramine, tetraethylenepentamine, dipropylenetriamine, polyethyleneimine, N-methyl-2,2'-diaminodiethylamine, N-acetylethylenediamine, and 1,2-bis(2-aminoethoxyethane). Any substance is usable insofar as it is an amino group.

(Quaternary Ammonium Group)

A quaternary ammonium group is a positively charged substituent represented by $NR_4^+$. Examples of it include groups represented by the following chemical formula (5) or (6).

[Chemical formula 5]

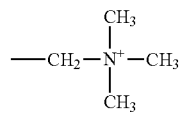

(5)

[Chemical formula 6]

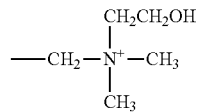

(6)

(Exchange Capacity and Zeta Potential)

Exchange capacity is used as one indicator showing the intensity of the cationic property. The exchange capacity of the adsorbent having the cationic functional groups is preferably 0.05 mEq or more, more preferably 0.5 mEq or more, per mL of the water insoluble carrier from the standpoint of achieving high adsorption performance. As another indicator for evaluating the cationic property, zeta potential can also be used preferably. When this zeta potential is used as an evaluation indicator, it is required to be 0 mV or more.

The exchange capacity can be measured in the following procedure. First, weigh an adsorbent and transfer it to a filtration tube by using demineralized water. Pour 1 mol/L-NaOH and demineralized water in the filtration tube successively, regenerate the resin, and wash. Then, pour 5% NaCl and receive an effluent in a 200-mL measuring flask until it becomes a constant volume. The exchange capacity can be determined by titrating the effluent with 0.1 mol/L-HCl while using a methyl red/methylene blue mixed indicator, but a measurement method is not limited to it.

The zeta potential of the surface of the adsorbent can be measured using, for example, streaming potential measurement. This streaming potential measurement is a method of determining the zeta potential by filling a space between a pair of streaming potential measurement electrodes with a solid sample such as powder or fiber, permeating a flowing liquid through the filled layer, and measuring a potential difference, that is, a streaming potential generated between the electrodes. The measurement method is however not limited to it.

(Histone)

Histones are DNA-bound proteins present in a liquid derived from a living-organism and they include Histone H1, Histone H2A, Histone H2B, Histone H3, and Histone H4. For the treatment of SIRS or the like, Histone H3 and Histone H4 are preferably removed from the liquid derived from the living-organism.

(Liquid Derived from Living-Organism)

The liquid derived from the living-organism embraces all of liquids derived from the living body and liquids containing a component derived from the living body. Specific examples include body liquids such as blood, plasma, serum, and ascites, and cell culture media.

The liquid derived from the living-organism may be brought into contact with the adsorbent of the present invention in various manners. Examples include a method of pouring the blood or ascites collected from a patient in a blood bag filled with the adsorbent of the present invention and causing histones in the blood or ascites of the patient to adsorb to it in the bag; and a method of circulating the blood through a device filled with the adsorbent of the present invention. The blood is not required to be whole blood and the plasma separated from the blood may be treated. The blood thus treated may be returned to the patient or may be stored in the blood bag as needed.

Examples of the method when a cell culture medium is used include a method of putting a collected culture medium in a bag filled with the adsorbent of the present invention and causing histones in the culture medium to adsorb to it in this bag; and a method of circulating the culture medium through a device filled with the adsorbent of the present invention. As the culture medium, a supernatant of the culture medium obtained by separating cells may be treated. The culture medium thus treated may be used for cell culturing again.

(Device)

FIG. 1 is a cross-sectional view showing one embodiment of a device. A device 100 is a module connected to, for example, an extracorporeal blood circulation circuit. This container is formed by screw-fitting a cap 150 having an inlet port 140 to one-end opening portion of a column 110 via a packing 130 in which a filter 120 has been stretched and screw-fitting a cap 170 having an outlet port 160 to the other end opening portion of the column 110 via a packing 130' in which a filter 120' has been stretched. Further, a histone adsorbent layer 180 is formed by filling a space between the filters 120 and 120' with the adsorbent and thereby retaining the adsorbent.

The histone adsorbent layer 180 may be filled only with the adsorbent according to the present embodiment or another adsorbent may be mixed with or stacked on the adsorbent according to the present embodiment. As the another adsorbent, an adsorbent for a malignant substance such as cytokine, an adsorbent having a wide range of adsorption performance, or the like can be used. Synergistic effects by these adsorbents can be expected to produce wide clinical effects. The volume of the histone adsorption carrier layer 180 can be set at from 5 mL to 3000 mL. It is preferably from 50 mL to 1000 mL, more preferably from 100 mL to 500 mL from the standpoint of the histone adsorption volume and extracorporeal blood amount during extracorporeal circulation of the blood.

The module to be connected to the extracorporeal blood circulation circuit is placed in the extracorporeal blood circulation circuit so as to come into contact with a liquid derived from a living-organism to be treated. It can be used for the treatment of systemic inflammatory diseases.

Figure 2:
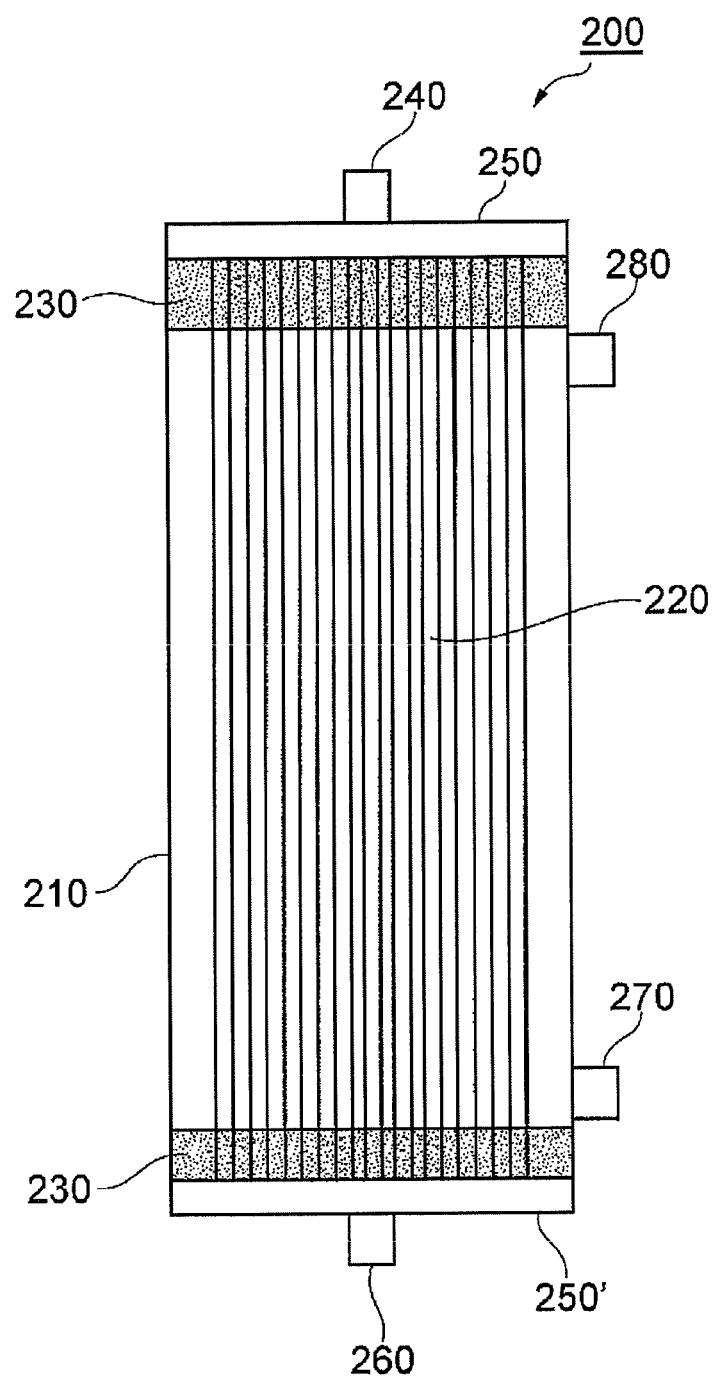
FIG. 2 is a cross-sectional view showing another embodiment of a device.

FIG. 2 is a cross-sectional view showing another embodiment of a device. A device 200 is a module connected to, for example, an extracorporeal blood circulation circuit. A column 210 has, at both ends thereof, an adsorbent 220 in hollow fiber form retained by a potting agent 230. The adsorbent 220 in hollow fiber form is opened at both end surfaces thereof. The hollow fiber adsorbent 220 is filled and retained by a cap 250 having an inlet port 240 and a cap 250' having an outlet port 260, each fitted in the column 210. The column 210 has, on the side surface thereof, a dialysate introduction port 270 and a dialysate delivery port 280.

When the device is used for therapeutic apheresis through extracorporeal blood circulation, the blood led from a body to be treated is introduced from the inlet port 240, is allowed to pass through the hollow fiber adsorbent 220, and is returned into the body to be treated through the outlet port 260. In such a manner, therapeutic apheresis can be achieved through extracorporeal blood circulation. During the extracorporeal blood circulation, dialysis can be performed by introducing a dialysate from the dialysate introduction port 270, leading the dialysate out from the dialysate delivery port 280, and thus circulating the dialysate in the device 200. This circulation of the dialysate is not always necessary and the dialysate introduction port 270 and the dialysate delivery port 280 may be opened. In this case, blood filtration is performed. In addition, therapeutic apheresis through extracorporeal blood circulation can be performed by blocking the dialysate introduction port 270 and the dialysate delivery port 280 with a stopper or the like to suppress blood filtration.

The adsorbent and device according to the present embodiment can be used effectively for suppressing or treating systemic inflammation in histone-mediated diseases. Specific examples of the disease include sepsis, septic shock, disseminated intravascular coagulation (DIC) syndrome, toxicogenic shock syndrome, ischemia-reperfusion injury, adult respiratory distress syndrome (ARDS), Paget's disease, osteoporosis, multiple myeloma, acute and chronic myelocytic leukemia, pancreatic β cell disruption, inflammatory intestinal disease, psoriasis, Crohn's disease, ulcerative colitis, anaphylaxia, contact dermatitis, asthma, myopathy, cachexia, Reiter's syndrome, type 1 and type 2 diabetes, bone resorption, graft versus host reaction, atherosclerosis, cerebral trauma, multiple sclerosis, cerebral malaria, and fever- or infection-induced muscle pain.

(Treatment Method)

Examples of a treatment method using the adsorbent and the device for purifying a liquid derived from a living-organism according to the present embodiment include a method of connecting the device for purifying a liquid derived from a living-organism of the present invention to a patient via a blood circuit, allowing the blood taken out from the patient to pass through the device for purifying a liquid derived from a living-organism of the present invention to reduce a histone content in the blood, returning the resulting blood to the patient, and thereby treating systemic inflammatory response syndrome.

It is also possible to separate the blood taken out from the blood of a patient into a blood cell component and a plasma component by using a plasma separation membrane, allow the separated plasma to pass through the liquid derived from living-organism purification device of the present invention to reduce a histone content in the plasma, return it to the patient, and thereby treat systemic inflammatory response syndrome.

The above-described adsorbent and device according to the present embodiment may be used in combination with another body liquid treatment method or another medical device. Examples of the another body liquid treatment method and medical device include continuous renal replacement therapy (CRRT), plasma exchange, peritoneal dialysis, plasma separator, hemofilter, artificial heart-lung machine, and ECMO.

The above-described adsorbent and device according to the present embodiment are suited for use in a treatment method including allowing a liquid derived from a living-organism and containing histone to pass through it and obtaining a liquid derived from a living-organism discharged from a device outlet and having a reduced histone content.

When the adsorbent of histone according to the present embodiment is brought into contact with a liquid derived from a living-organism or the like for a predetermine time, an adsorption rate of histone before and after this treatment can be determined from the following formula.

Histone adsorption rate (%)=$(C_o-C)/C_o \times 100$ $C_o$: histone concentration in a solution before treatment
$C$: histone concentration in a solution after treatment Examples of a method of bringing the adsorbent according to the present embodiment into contact with a liquid derived from a living-organism or the like in order to evaluate a histone adsorption rate include a method of adding lipopolysaccharide (LPS) derived from *Escherichia coli* to the blood collected from a healthy volunteer, shaking the resulting mixture in a shaker, centrifuging it by a centrifuge to obtain a supernatant as a plasma sample, mixing the plasma sample thus obtained with the adsorbent in a tube made of polypropylene (PP), and shaking the tube in a shaker.

Examples also include a method of adding lipopolysaccharide derived from *E. coli* to the blood collected from a healthy volunteer, shaking the resulting mixture in a shaker, and causing, using a syringe pump, the blood to pass through an adsorbent-filled column made by filling a laboratory column (MoBiTec) having an inner diameter of 9 mm and a volume of 2.5 mL with the adsorbent.

Further, examples of a method of bringing the blood into contact with a full module having a scale equal to that of the product include a method of adding *E. coli*-derived lipopolysaccharide to the blood collected from a healthy volunteer, shaking the resulting mixture in a shaker, and circulating the resulting blood through a device filled with the adsorbent as shown in FIG. 1 by using a Perista™ pump. In this method, the volume of the entire circulation circuit including the device is preferably made smaller in order to reduce the using amount of the blood.

The present invention will hereinafter be described specifically by Examples, but it is not limited to or by them.

Example 1

(Preparation and Evaluation of Adsorbent)

Ultrafiltered (UF) water was added to a strongly basic anion exchange resin (Diaion; product of Mitsubishi Chemical) having a trimethylammonium group and containing a styrene divinylbenzene-based copolymer. The resulting mixture was heated to 95° C. and was washed with hot water for 22 hours or more. Next, primary coating was performed by immersing the strongly basic anion exchange resin for four hours in a coating solution of p-HEMA as a biocompatible polymer dissolved in ethanol to give a polymer concentration of 0.75%. Then, hot wind drying at 70° C. was performed overnight, followed by heating and crosslinking with hot wind at 120° C. for two hours. Then, secondary coating of the primary-coated strongly basic anion exchange resin cooled with wind was performed with the p-HEMA coating solution in a procedure similar to that used in the primary coating. The secondary-coated strongly basic anion exchange resin was cooled with wind to obtain an adsorbent A.

(Plasma Histone H3 Adsorption Test)

To the blood collected from a healthy volunteer was added lipopolysaccharide (LPS) derived from *Escherichia coli* 0127: B8 (product of Sigma-Aldrich) to give a concentration of 0.1 μg/ml. The resulting mixture was shaken at 39° C. for 24 hours in a shaker. Then, the resulting mixture was centrifuged at 2000 g for 10 minutes using a centrifuge and a supernatant was obtained as a plasma sample. In a tube made of polypropylene (PP), 3 ml of the plasma sample thus obtained and 0.5 ml of the adsorbent A were mixed, followed by shaking at 39° C. for one hour in a shaker. The tube made of PP after shaking was centrifuged at 2000 g for one minute in a centrifuge and a supernatant was obtained as a plasma sample after contact with the carrier.

(Evaluation of Histone H3 Removal Performance)

A Histone H3 adsorption rate of the adsorbent A was calculated using the plasma sample obtained after brought into contact with a carrier. The calculation formula of the Histone H3 adsorption rate is shown below, wherein A represents a Histone H3 adsorption rate (%), $C_o$ represents a Histone H3 concentration before treatment with the adsorbent, and $C_A$ represents a Histone H3 concentration after treatment with the adsorbent. The same Histone H3 adsorption rate calculation formula was used in the following Examples 2 to 9 and Comparative Examples 1 to 3. The concentration of Histone 3 was measured using EpiQuik (registered trademark) Total Histone H3 Quantification Kit (product of EPIGENTEK). The results are shown in Table 1.

$$A = \frac{C_0 - C_A}{C_0} \times 100 \quad \text{[Formula 1]}$$

(Measurement of Antithrombogenicity)

Antithrombogenicity measurement was performed with an amount of blood cells attached to the surface of an adsorption carrier as an indicator. More specifically, heparin was added to the blood of a healthy subject to give a final concentration of 1 IU/ml. The resulting blood was added to 0.5 ml of a resin wetted with physiological saline. The resulting mixture was left to stand at 37° C. for 30 minutes. Then, the adsorbent separated and washed with physiological saline was macroscopically observed. The results are shown in Table 1.

Example 2

(Synthesis of Biocompatible Polymer)

Polymerization was performed by using ethanol as a polymerization solvent and adding dropwise an ethanol solution in which polymerizable monomers and a diazo-based initiator had been dissolved while stirring at 78° C. in a nitrogen atmosphere. With regard to the polymerizable monomers to be mixed, 25 mol % of methyl methacrylate (which will hereinafter be abbreviated as "MMA") as a hydrophobic polymerizable monomer, 13 mol % of dimethylaminoethyl methacrylate (which will hereinafter be abbreviated as "DM") as a polymerizable monomer having a basic nitrogen-containing portion, and 62 mol % of 2-hydroxyethyl methacrylate (which will hereinafter be abbreviated as "HEMA") as a monomer containing a protonic neutral hydrophilic portion were mixed. The resulting polymerization liquid was purified with excess water, followed by drying under reduced pressure to obtain a synthetic polymer A.

(Preparation and Evaluation of Adsorbent)

UF water was added to a strongly basic anion exchange resin (Diaion; product of Mitsubishi Chemical). The resulting mixture was heated to 95° C. and was washed with hot water for 22 hours or more. Next, primary coating was performed by immersing the strongly basic anion exchange resin in a coating solution of the above-described synthetic polymer A for four hours. Then, hot wind drying was performed overnight at 70° C., followed by heating and crosslinking with hot wind at 120° C. for two hours. Secondary coating of the primary-coated strongly basic anion exchange resin cooled with wind was performed with a coating solution of the synthetic polymer A in a procedure similar to that of the primary coating. The secondary-coated strongly basic anion exchange resin was cooled with wind to obtain an adsorbent B. The results of an adsorption test made similar to that of Example 1 by using the adsorbent B are shown in Table 1.

Example 3

(Synthesis of Biocompatible Polymer)

Polymerization, purification, and drying were performed under conditions similar to those of Example 2 except that the polymerizable monomers DM and HEMA were mixed at a mixed ratio of 3 mol % and 97 mol %, respectively, to obtain a synthetic polymer B.

(Preparation and Evaluation of Adsorbent)

UF water was added to a strongly basic anion exchange resin (Diaion; product of Mitsubishi Chemical). The resulting mixture was heated to 95° C. and was washed with hot water for 22 hours or more. Next, primary coating was performed by immersing the strongly basic anion exchange resin in a coating solution of the synthetic polymer B for four hours. Then, hot wind drying was performed overnight at 70° C., followed by heating and crosslinking with hot wind at 120° C. for two hours. Secondary coating of the primary-coated strongly basic anion exchange resin cooled with wind was performed with a coating solution of the synthetic polymer B in a procedure similar to that of the primary coating. The secondary-coated strongly basic anion exchange resin was cooled with wind to obtain an adsorbent C. The results of an adsorption test similar to that of Example 1 made using the adsorbent C are shown in Table 1.

Example 4

(Preparation and Evaluation of Adsorbent)

Activated carbon beads (product of Kureha) were washed with 0.1N hydrochloric acid, washed further with UF water, and then washed with warm water of from 60 to 65° C. for 40 hours or more. Next, primary coating was performed by immersing the activated carbon beads for four hours in a coating solution obtained by dissolving p-HEMA in ethanol to give a polymer concentration of 0.75%. Then, hot wind drying was performed overnight at 70° C., followed by heating and crosslinking with hot wind at 120° C. for two hours. Secondary coating of the primary-coated activated carbon beads cooled with wind was then performed with the p-HEMA coating solution in a procedure similar to that of the primary coating. The secondary-coated activated carbon beads were cooled with wind to obtain an adsorbent D. The results of an adsorption test similar to that of Example 1 made using the adsorbent D are shown in Table 1.

Example 5

(Preparation and Evaluation of Adsorbent)

Activated carbon beads (product of Kureha) were washed with 0.1N hydrochloric acid, washed further with UF water, and then washed with warm water of from 60 to 65° C. for 40 hours or more. Next, primary coating was performed by immersing the activated carbon beads for four hours in a coating solution of the synthetic polymer A. Then, hot wind drying was performed overnight at 70° C., followed by heating and crosslinking with hot wind at 120° C. for two hours. Secondary coating of the primary-coated activated carbon beads cooled with wind was then performed with the coating solution of the synthetic polymer A in a procedure similar to that of the primary coating. The secondary-coated activated carbon beads were cooled with wind to obtain an adsorbent E. The results of an adsorption test similar to that of Example 1 made using the adsorbent E are shown in Table 1.

Example 6

(Preparation and Evaluation of Adsorbent)

Activated carbon beads (product of Kureha) were washed with 0.1N hydrochloric acid, washed further with UF water, and then washed with warm water of from 60 to 65° C. for 40 hours or more. Next, primary coating was performed by immersing the activated carbon beads for four hours in a coating solution of the synthetic polymer B. Then, hot wind drying was performed overnight at 70° C., followed by heating and crosslinking with hot wind at 120° C. for two hours. Secondary coating of the primary-coated activated carbon beads cooled with wind was then performed with the coating solution of the synthetic polymer B in a procedure similar to that of the primary coating. The secondary-coated activated carbon beads were cooled with wind to obtain an adsorbent F. The results of an adsorption test similar to that of Example 1 made using the adsorbent F are shown in Table 1.

Example 7

(Preparation and Evaluation of Adsorbent)

An adsorbent G was obtained by coating, with the synthetic polymer A, a PET nonwoven fabric having an average fiber diameter of 1.3 μm and used as a material. The results of an adsorption test similar to that of Example 1 made using the adsorbent G are shown in Table 1.

Example 8

(Synthesis of Biocompatible Polymer)

Polymerization, purification, and drying were performed under conditions similar to those of Example 2 except that the polymerizable monomers MMA, DM, and HEMA were mixed at a mixed ratio of 30 mol %, 10 mol %, and 60 mol %, respectively, to obtain a synthetic polymer C.

(Preparation and Evaluation of Adsorbent)

An adsorbent H was obtained by coating, with the synthetic polymer C, a polyethylene terephthalate (PET) nonwoven fabric used as a material. The results of an adsorption test similar to that of Example 1 made using the adsorbent H are shown in Table 1.

Example 9

(Preparation and Evaluation of Adsorbent)

An adsorbent I was obtained by coating, with the synthetic polymer B, a polyethylene terephthalate (PET) nonwoven fabric used as a material. The results of an adsorption test similar to that of Example 1 made using the adsorbent are shown in Table 1.

Comparative Example 1

An adsorption test was made using an adsorption carrier L similar to that of Example 1 except that a strongly basic anion exchange resin similar to that of Example 1 had not been subjected to P-HEMA coating. The results are shown in Table 1.

Comparative Example 2

An adsorption test was made using an adsorption carrier M similar to that of Example 4 except that activated carbon beads similar to those of Example 4 had not been subjected to P-HEMA coating. The results are shown Table 1.

Comparative Example 3

An adsorption test was made using an adsorption carrier N similar to that of Example 7 except that a PET nonwoven fabric similar to that of Example 7 had not been coated with the solution of the synthetic polymer A. The results are shown in Table 1.

cells attached thereto (had low antithrombogenicity) and did not satisfy the minimum biocompatibility required for an adsorption carrier for histone removal device.

Example 10

(Preparation and Evaluation of Hollow Fiber Adsorbent)

A device was prepared by allowing both ends of a hollow fiber membrane made of polysulfone and polyvinylpyrrolidone to adhere with an epoxy adhesive so that it had an effective length of 17 cm and membrane surface area of 100 mm$^2$ (corresponding to 100 filaments because a hollow fiber membrane having an inner diameter of 185 μm was used). The synthetic polymer A was moved through the device from a blood inlet port of the device at 5 [mL/min] for 20 seconds to coat the interior surface of the hollow fiber. A device including an adsorbent J was thus prepared.

(Plasma Histone H3 Adsorption Test)

To the blood collected from a healthy volunteer was added lipopolysaccharide (LPS) derived from *Escherichia coli* 0127: B8 (product of Sigma-Aldrich) to give a concentration of 0.1 μg/ml. The resulting mixture was shaken at 39° C. for 24 hours in a shaker. Then, the resulting mixture was centrifuged at 2000 g for 10 minutes using a centrifuge and a supernatant was obtained as a plasma sample. The plasma sample thus obtained (10 ml) was circulated through the device including the adsorbent J at a flow rate of 1.2 ml/min at 39° C. for 60 minutes by using a Perista™ pump. Then, the plasma thus circulated was obtained as a plasma sample after contact with carrier.

(Evaluation of Histone H3 Removal Performance)

A Histone H3 adsorption rate of the resulting plasma sample after contact with carrier was calculated after the treatment. The calculation formula of the Histone H3

TABLE 1

| | Adsorbent | Carrier | Coating polymer | Carrier form | Average particle size (μm) | Average fiber diameter (μm) | Histone H3 adsorption rate (%) | Macroscopic observation results |
|---|---|---|---|---|---|---|---|---|
| Example 1 | A | Styrene divinylbenzene | p-HEMA | Particle | 400 | — | 98 | No blood cell attached |
| Example 2 | B | Styrene divinylbenzene | Synthetic polymer A | Particle | 400 | — | 99 | |
| Example 3 | C | Styrene divinylbenzene | Synthetic polymer B | Particle | 400 | — | 98 | |
| Example 4 | D | Activated carbon | p-HEMA | Particle | 700 | — | 15 | |
| Example 5 | E | Activated carbon | Synthetic polymer A | Particle | 700 | — | 80 | |
| Example 6 | F | Activated carbon | Synthetic polymer B | Particle | 700 | — | 30 | |
| Example 7 | G | PET nonwoven fabric | Synthetic polymer A | Nonwoven fabric | — | 1.3 | 97 | |
| Example 8 | H | PET nonwoven fabric | Synthetic polymer C | Nonwoven fabric | — | 1.3 | 80 | |
| Example 9 | I | PET nonwoven fabric | Synthetic polymer B | Nonwoven fabric | — | 1.3 | 37 | |
| Comp. Ex. 1 | L | Styrene divinylbenzene | None | Particle | 400 | — | 98 | Blood cell attached |
| Comp. Ex. 2 | M | Activated carbon | None | Particle | 700 | — | 15 | |
| Comp. Ex. 3 | N | PET nonwoven fabric | None | Nonwoven fabric | — | 1.3 | 0 | |

The results of Table 1 show that the adsorption carriers A, B, C, D, E, F, G, H, and I having a carrier surface coated with the biocompatible polymer had good antithrombogenicity and at the same time, removed Histone H3. They show, on the other hand, that the adsorption carriers L, M, and N not coated with a biocompatible polymer each had many blood adsorption rate is shown below, wherein $A_H$ represents a Histone H3 adsorption rate (%), $C_{HO}$ represents a Histone H3 concentration before treatment with a hollow fiber, and $C_{HA}$ represents a Histone H3 concentration after treatment with the coated hollow fiber. The same calculation formula of the Histone H3 adsorption rate was used in the following Example 11 and Comparative Examples 4 and 5. The concentration of Histone 3 was measured using EpiQuik (registered trademark) Total Histone H3 Quantification Kit (product of EPIGENTEK). The results are shown in Table 2.

$$A_H = \frac{C_{H0} - C_{HA}}{C_{H0}} \times 100 \quad \text{[Formula 2]}$$

(Measurement of Antithrombogenicity)

Antithrombogenicity measurement was performed with an amount of blood cells attached to the surface of a hollow fiber carrier as an indicator. More specifically, heparin was added to the blood of a healthy subject to give a final concentration of 1 IU/ml. The resulting blood was circulated, with a Perista™ pump, through a device including the adsorbent J filled with physiological saline at a flow rate of 1.2 ml/min at 37° C. for 60 minutes. Then, the blood inside the hollow fiber was washed with physiological saline. The device was broken down. The hollow fiber taken out from it was immersed in 2.5% glutaraldehyde to immobilize the blood cells. The resulting hollow fiber was immersed successively in 25%, 50%, 60%, 70%, 80%, 90%, and 99% ethanol (product of Wako Pure Chemicals) solutions and after dehydration, the hollow fiber was immersed in t-butyl alcohol (product of Wako Pure Chemicals). After sufficient removal of t-butyl alcohol from the hollow fiber, the resulting hollow fiber was frozen and freeze-dried overnight. The freeze-dried hollow fiber was sliced at a certain angle, followed by vapor deposition by an ion sputter to obtain a hollow fiber SEM sample. The sample was subjected to SEM observation to evaluate attachment of blood cells. The results are shown in Table 2.

Example 11

A device was prepared by allowing both ends of a hollow fiber membrane made of polysulfone and polyvinylpyrrolidone to adhere with an epoxy adhesive so that it had an effective length of 17 cm and a membrane surface area of 100 mm² (corresponding to 100 filaments because a hollow fiber membrane having an inner diameter of 185 μm was used). The synthetic polymer B was moved through the device from a blood inlet port of the device to coat the interior surface of the hollow fiber with the synthetic polymer B to prepare a device including an adsorbent K. The results of an adsorption test made using the device including this adsorbent K are shown in Table 2.

Comparative Example 4

(Preparation and Evaluation of Hollow Fiber Adsorbent)

A device was manufactured by allowing both ends of a hollow fiber membrane made of polysulfone and polyvinylpyrrolidone to adhere with an epoxy adhesive so that it had an effective length of 17 cm and a membrane surface area of 100 mm² (corresponding to 100 filaments because a hollow fiber membrane having an inner diameter of 185 μm was used). The results of an adsorption test made using the device including this adsorbent O are shown in Table 2.

Comparative Example 5

(Preparation and Evaluation of Hollow Fiber Adsorbent)

A device was prepared by allowing both ends of a hollow fiber membrane made of polysulfone and polyvinylpyrrolidone to adhere with an epoxy adhesive so that it had an effective length of 17 cm and a membrane surface area of 100 mm² (corresponding to 100 filaments because a hollow fiber membrane having an inner diameter of 185 μm was used). The results of an adsorption test made using the device including this adsorbent P are shown in Table 2.

TABLE 2

| | Adsorbent | Carrier | Coating polymer | Carrier form | Average hollow fiber inner diameter (μm) | Histone H3 adsorption rate (%) | SEM observation results |
|---|---|---|---|---|---|---|---|
| Example 10 | J | Polysulfone hollow fiber | PVP + synthetic polymer A | Hollow fiber | 185 | 12 | No blood cell attached |
| Example 11 | K | Polysulfone hollow fiber | PVP + synthetic polymer B | Hollow fiber | 185 | 12 | |
| Comp. Ex. 4 | O | Polysulfone hollow fiber | None | Hollow fiber | 185 | 5 | Blood cell attached |
| Comp. Ex. 5 | P | Polysulfone hollow fiber | PVP | Hollow fiber | 185 | 0 | No blood cell attached |

The results of Table 2 show that the device including the adsorbent J or adsorbent K having a carrier surface coated with the biocompatible polymer showed good antithrombogenicity and at the same time, removed Histone H3. They show, on the other hand, the device including the adsorbent O not coated with a biocompatible polymer had many blood cells attached thereto (had low antithrombogenicity) and did not satisfy the minimum biocompatibility required for a histone removal device. Further, the device including the adsorbent P coated with cationic functional group-free PVP showed high antithrombogenicity but did not adsorb histone to the device.

Example 12

(Water-Based Histone H4 Adsorption Test)

A solution (0.2 mL) was prepared in a PP tube by adding a standard product (Histone H4 (initial concentration: 50 μg/mL) included in EpiQuik (registered trademark) Total Histone H4 Quantification Kit (product of EPIGENTEK) to physiological saline. To the tube was added 0.1 mL of the adsorbent A, followed by shaking at 39° C. for one hour using a shaker. The PP tube after shaking was centrifuged at 2000 g for one minute by using a centrifuge and a supernatant was obtained as a plasma sample after contact with carrier.

(Evaluation of Histone H4 Removal Performance)

A Histone H4 adsorption rate of the adsorbent A was calculated using the resulting plasma sample after contact with carrier. The calculation formula of the Histone H4 adsorption rate is shown below, wherein $A_4$ represents a Histone H4 adsorption rate (%), $C_{40}$ represents a Histone H4 concentration before treatment with adsorbent, and $C_{4A}$ represents a Histone H4 concentration after treatment with the adsorbent. The same histone H4 adsorption rate calculation formula was used also in the following Examples 13 and 14 and Comparative Example 6. The concentration of Histone H4 was measured using EpiQuik (registered trademark) Total Histone H4 Quantification Kit (product of EPIGENTEK). The results are shown in Table 3.

$$A_{H4} = \frac{C_{40} - C_{4A}}{C_{40}} \times 100 \qquad \text{[Formula 3]}$$

Example 13

The results of an adsorption test similar to that of Example 12 made using the adsorbent D are shown in Table 3.

Example 14

The results of an adsorption test similar to that of Example 12 made using the adsorbent G are shown in Table 3.

Comparative Example 6

(Water-Based Histone H4 Adsorption Test)

A solution (0.2 mL) was prepared in a PP tube by adding a standard product (Histone H4 (initial concentration: 50 μg/mL) included in EpiQuik (registered trademark) Total Histone H4 Quantification Kit (product of EPIGENTEK) to physiological saline. Without adding an adsorbent, the resulting solution was shaken at 39° C. for one hour by using a shaker. The PP tube after shaking was centrifuged at 2000 g for one minute by using a centrifuge and a supernatant was obtained as a plasma sample.

(Evaluation of Histone H4 Removal Performance)

A Histone H4 adsorption rate of each of the plasma samples thus obtained after treatment was calculated. The calculation formula of the Histone H4 adsorption rate is shown below. The concentration of Histone 4 was measured using EpiQuik (registered trademark) Total Histone H4 Quantification Kit (product of EPIGENTEK). The results are shown in Table 3.

The results of Table 3 show that the respective devices including the adsorbents A, D, and G having a carrier surface coated with a biocompatible polymer removed Histone H4. In Comparative Example 6, Histone H4 is presumed to adsorb to the PP tube nonspecifically.

INDUSTRIAL APPLICABILITY

The adsorbent and the device for purifying a liquid derived from a living-organism according to the present embodiment can remove Histone H3 from the liquid derived from a living-organism while having good biocompatibility so that they are useful for the treatment of diseases typified by SIRS that occur or worsen due to the presence of histones.

This device for purifying a liquid derived from a living-organism can be used for the treatment of SIRS and the like caused by histones. By bringing the adsorbent according to the present embodiment into contact with the liquid derived from a living-organism, histones in the liquid derived from a living-organism can be adsorbed to the adsorbent with good biocompatibility, histones can be removed from the liquid derived from the living-organism, and extracellular histones harmful for the living body can be removed so that it can be used effectively for suppressing or treating systemic inflammation in diseases caused by histones. Specific examples of such a disease include sepsis, septic shock, disseminated intravascular coagulation (DIC) syndrome, toxicogenic shock syndrome, ischemia-reperfusion injury, adult respiratory distress syndrome (ARDS), Paget's disease, osteoporosis, multiple myeloma, acute and chronic myelocytic leukemia, pancreatic 13 cell disruption, inflammatory intestinal disease, psoriasis, Crohn's disease, ulcerative colitis, anaphylaxia, contact dermatitis, asthma, myopathy, cachexia, Reiter's syndrome, type 1 and type 2 diabetes, bone resorption, graft versus host reaction, atherosclerosis, cerebral trauma, multiple sclerosis, cerebral malaria, and fever- or infection-induced muscle pain. In particular, they are suited for use for improvement of the clinical condition of systemic inflammatory response syndrome (SIRS) such as sepsis.

More specifically, they are suited for use in, as a method by extracorporeal blood circulation, extracorporeal circulation therapy including removing the blood from a patient, introducing the whole blood as is or plasma separated therefrom using a plasma separation (primary) membrane or centrifugal separation into, for example, the inlet port 140 of the device shown in FIG. 1, discharging it from the outlet port 160 and thereby returning the blood or plasma having a reduced histone content into the body of the patient.

The adsorbent and the device according to the present embodiment are also suited for use in a treatment method including causing a liquid derived from a living-organism

TABLE 3

| | Adsorbent | Carrier | Coating polymer | Carrier form | Average particle size (μm) | Average fiber diameter (μm) | Histone H4 adsorption rate (%) |
|---|---|---|---|---|---|---|---|
| Example 12 | A | Styrene divinylbenzene | p-HEMA | Particle | 400 | — | 65 |
| Example 13 | D | Activated carbon | p-HEMA | Particle | 700 | — | 55 |
| Example 14 | G | PET nonwoven fabric | Synthetic polymer A | Nonwoven fabric | — | 1.3 | 82 |
| Comp. Ex. 6 | — | — | — | — | — | — | 20 | and containing histone to pass through them and obtaining a liquid derived from a living-organism and discharged from the device outlet and having a reduced histone content.

Examples include a method of putting the blood or ascites collected from a patient in a blood bag filled with the adsorbent of the present invention and allowing, in this bag, histones in the blood or ascites of the patient to adsorb to the adsorbent. The blood is not limited to the whole blood and the plasma separated from the blood may be treated. The blood thus treated may be returned to the patient or may be stored in a blood bag as needed.

It is reported that histones have cytotoxicity. This device for purifying a liquid derived from a living-organism is suited for use for removing histones having cytotoxicity from the cell culture medium.

Examples include a method of putting a collected culture medium in a bag filled with the adsorbent of the present invention and allowing histones in the culture medium to adsorb to the adsorbent in this bag; and a method of circulating a culture medium through a device filled with the adsorbent of the present invention. After cells are separated from the culture medium, a supernatant of the culture medium may be treated. The culture medium thus treated may be used again for cell culturing. It is needless to say that the industrial application field of the present invention is not limited to the above-described ones.

REFERENCE SIGNS LIST 100, 200: device, 110, 210: column, 120, 120': filter, 130, 130': packing, 140, 240: inlet port, 150, 170, 250, 250': cap, 160, 260: outlet port, 180: systemic inflammation suppressing carrier layer, 220: carrier (adsorption carrier), 230: potting agent, 270: dialysate introduction port, 280: dialysate discharge port

What is claimed is:

1. A method for removing a histone from a liquid derived from a living-organism comprising contacting the liquid ex vivo with an adsorbent comprising a water insoluble carrier and a biocompatible polymer, the carrier being at least one selected from the group consisting of activated carbon, a polyester, and a polysulfone, or the carrier being modified with a cationic functional group, wherein in the contacting, the histone is adsorbed by the adsorbent to obtain a histone removed from the liquid.

2. The method according to claim 1, wherein the biocompatible polymer comprises a cationic functional group.

3. The method according to claim 1, wherein the carrier is in particle form, in non-woven fabric form, or in hollow fiber membrane form.

4. The method according to claim 1, wherein the carrier is polyethylene terephthalate or a styrene divinylbenzene-based copolymer, the carrier being modified with the cationic functional group.

5. The method according to claim 4, wherein the cationic functional group is an amino group.

6. The method according to claim 4, wherein the cationic functional group is a quaternary ammonium group.

7. The method according to claim 1, wherein the biocompatible polymer is a hydrophilic polymer.

8. The method according to claim 7, wherein the hydrophilic polymer is a hydroxyethyl methacrylate-based polymer.

9. The method according to claim 1, wherein the biocompatible polymer is a polymer containing 10 mol % or more of dimethylaminoethyl methacrylate.

10. The method according to claim 1, wherein the histone is Histone H3.

11. The method according to claim 1, wherein the adsorbent is housed in a housing and, in the contacting, the liquid is moved through the housing.

12. The method according to claim 11, wherein the liquid is a body liquid.

13. The method according to claim 12, wherein the body liquid is at least blood.

14. The method according to claim 11, wherein the housing further comprises an inlet and an outlet, the inlet and the outlet being on opposite sides of the adsorbent in the housing, wherein, in the contacting, the liquid is moved through the inlet and the outlet.

15. A method for treating systemic inflammatory response syndrome in a subject in need of treatment thereof comprising:
    contacting blood or plasma from the subject ex vivo with an adsorbent comprising a water insoluble carrier and a biocompatible polymer, the carrier being at least one selected from the group consisting of activated carbon, a polyester, and a polysulfone, or the carrier being modified with a cationic functional group, wherein the blood or plasma comprises a histone and, in the contacting, the histone is removed from the blood or plasma to obtain a blood or plasma having reduced histone content than the histone content of the blood or plasma prior to the contacting; and
    infusing the subject with the blood or plasma having reduced histone content.

16. The method according to claim 15, wherein the adsorbent is housed in a housing and, in the contacting, the blood or plasma is moved through the housing.

17. The method according to claim 16, wherein the housing further comprises an inlet and an outlet, the inlet and the outlet being on opposite sides of the adsorbent in the housing, wherein, in the contacting, the blood or plasma is moved through the inlet and the outlet.

* * * * *